(12) United States Patent
Brown et al.

(10) Patent No.: US 7,674,408 B2
(45) Date of Patent: Mar. 9, 2010

(54) CHANNELED BIOMEDICAL FOAMS AN METHOD FOR PRODUCING SAME

(75) Inventors: Kelly R. Brown, Hillsborough, NJ (US); Mora C. Melican, Bridgewater, NJ (US); Iksoo Chun, Flemngton, NJ (US)

(73) Assignee: Ethicon, Inc., Somerville, NJ (US)

( * ) Notice: Subject to any disclaimer, the term of this patent is extended or adjusted under 35 U.S.C. 154(b) by 902 days.

(21) Appl. No.: 11/230,220

(22) Filed: Sep. 19, 2005

(65) Prior Publication Data
US 2006/0069435 A1    Mar. 30, 2006

Related U.S. Application Data

(62) Division of application No. 10/106,007, filed on Mar. 25, 2002, now abandoned.

(51) Int. Cl.
    *C08J 9/26* (2006.01)
(52) U.S. Cl. .............. 264/49; 264/28; 264/41; 264/101; 264/237; 264/348; 424/426; 424/486; 521/61; 521/63
(58) Field of Classification Search .......... 264/28, 264/41, 101, 49, 237, 348; 424/426, 486; 521/61, 63
See application file for complete search history.

(56) References Cited

U.S. PATENT DOCUMENTS

| | | | |
|---|---|---|---|
| 5,514,378 A | 5/1996 | Mikos et al. | |
| 5,723,508 A | 3/1998 | Healy et al. | |
| 6,103,255 A | 8/2000 | Levene et al. | |
| 6,267,916 B1 | 7/2001 | Meyering et al. | |
| 6,306,424 B1 * | 10/2001 | Vyakarnam et al. | 424/426 |

FOREIGN PATENT DOCUMENTS

| | | |
|---|---|---|
| EP | 1 064 958 A1 | 1/2001 |
| WO | WO 94 25079 A | 10/1994 |
| WO | WO 99/25391 A2 | 5/1999 |
| WO | WO 00/09043 A1 * | 2/2000 |
| WO | WO 00/62829 S1 | 10/2000 |

OTHER PUBLICATIONS

EPO Search Report dated Aug. 12, 2003, for EPO application No. EP 03 25 1824.
Jackson, et al., "The Phase Behavior and Gelation of a Rod-Like Polymer in Solution and Implications for MIcrocellular Foam Morphology", Poymer, 1990, vol. 31. pp. 1070-1084.
Schugens, Ch., et al., "Polylactide Macroporos Biodegradable Implants for Cell Transplantatoin,. II. Preparation of Polylactide Foams by Liquid-Liquid Phase Separation", Journal of Biomedical Materials, vol. 30, pp. 449-461.
Schoof, H., et al. "Control of Pore Stucture and Size in Freeze-Dried Collagen Sponge", pp. 352-357.

* cited by examiner

*Primary Examiner*—Joseph S. Del Sole
*Assistant Examiner*—Timothy Kennedy
(74) *Attorney, Agent, or Firm*—Emil Richard Skula

(57) ABSTRACT

The present invention provides a biomedical, biocompatible, polymeric foam scaffold suitable for use in the repair and regeneration of tissue and which contains located therein a network of, branched channels that are effective to encourage and facilitate vascularization and tissue growth within the scaffold and to methods for making such biomedical scaffolds.

9 Claims, 2 Drawing Sheets

CHANNELED BIOMEDICAL FOAMS AN METHOD FOR PRODUCING SAME

This is a divisional application of U.S. Ser. No. 10/106,007, filed Mar. 25, 2002 now abandoned.

FIELD OF THE INVENTION

The present invention relates to biomedical porous polymeric foam scaffolds useful for tissue repair and regeneration and methods for preparing same.

BACKGROUND OF THE INVENTION

Over the past two decades, the field of tissue engineering has focused on the repair and reconstruction of tissue utilizing scaffolds, both as a means to culture cells in vitro for subsequent implantation in vivo and as an acellular implant to encourage tissue ingrowth and incorporation. Scaffolds seeded and cultured with cells are utilized to deliver and/or direct cells to desired sites in the body, to define a potential space for engineered tissue, and to guide the process of tissue development. In the case of cell culture, cell transplantation, on or from scaffolds, has been explored for the regeneration of skin, nerve, liver, pancreas, cartilage, adipose and bone tissue, using various biological and synthetic materials.

Acellular scaffolds have also been developed for promoting the attachment and migration of cells from the surrounding living tissue to the surface and interior of the scaffold. In these cases, bioabsorbable materials are useful in order to provide a substrate for incipient tissue growth and subsequent degradation and elimination from the area leaving behind newly regenerated tissue. Examples of such materials include poly(lactic acid) (PLA), poly(caprolactone) (PCL), poly(glycolic acid) (PGA), poly(dioxanone) (PDO), poly(trimethylene carbonate) (TMC), and their copolymers and blends.

Scaffolds, whether acellular or seeded, have certain requirements with regards to the penetration of the scaffold by cells and the nutrient flow to cells. Scaffolds with pores of diameters up to 500 microns provide sufficient open space for the formation of functional tissue, but lack the means necessary to provide sufficient infiltration of cells, diffusion of nutrients and oxygen to the cells, removal of metabolic waste away from the cells, and to guide the cells and fluids.

Several attempts to provide scaffolds with architectures to improve the diffusion of nutrients through the scaffold have been made in the recent past. These include bimodal porous structures that enhance the available surface area and internal volume of the scaffold. These structures were created using leachable particles incorporated into either a polymer or a polymer solution. In the case of the polymer solution, freeze drying was used to create a polymer foam embedded with leachable particles. The foam was then subjected to a subsequent step in which the particles were leached out of the system to create a second set of pores.

Alternatively, biocompatible porous polymer membranes were prepared by dispersing salt particles in a biocompatible polymer solution. The solvent was evaporated and the salt particles were leached out of the membrane by immersing the membrane in a solvent for the salt particles. A three-dimensional porous structure was then manufactured by laminating the membranes together to form the desired shape.

Others have circumvented the use of leachable particles to form porous membranes of various pore diameters by casting a layer of polymer solution on a substrate and submerging the layer/substrate in a non-solvent for the polymer. This created a porous a polymer structure. The cast layers were laminated to achieve gradients in porosity in the three-dimensional structure.

Still others have used a rigid-coil/flexible-coil block copolymer mixed with a solvent that selectively solubilized one of the blocks. The other block of the copolymer was permitted to self-assemble into organized mesostructures. The solvent was then evaporated, leaving the structure mesoporous.

The field of tissue engineering to repair and reconstruct tissue has utilized scaffolds to encourage tissue ingrowth and incorporation, scaffolds in the form of porous polymer foams. The morphology of foams has progressed from random to controlled formation, but the controlled morphology has resulted either in a monomodal, isotropic distribution of pores through spinodal decomposition of polymer solvent mixtures or in the production of uniaxial channels in the foam. There remains a need for biodegradable porous polymer scaffolds for tissue engineering that have an architecture providing for the effective and thorough distribution of fluids and nutrients necessary for tissue growth. In addition, it would be advantageous to be able to produce this scaffold by way of a method that does not require any manipulation of the material post-processing.

SUMMARY OF THE INVENTION

The present invention provides a biomedical, biocompatible, foam scaffold suitable for use in the repair and regeneration of tissue that comprises a network of branched, channels effective to encourage and facilitate vascularization and tissue growth therein and a process for making the biomedical scaffolds. The process comprises preparing a homogenous mixture of a synthetic, biocompatible polymer, a solvent in which the polymer is soluble and a non-solvent in which the polymer is not soluble. The solvent and non-solvent are miscible and the freezing point of the non-solvent is higher than the freezing point of the solvent. The homogeneous mixture is placed in a mold and cooled to a temperature effective to freeze the non-solvent. This temperature is maintained for a time effective to allow the non-solvent to phase-separate from the mixture. The mixture is then cooled to a temperature effective to form a solid, and the solvent and non-solvent are removed from the solid to provide a biocompatible, porous scaffold suitable for use in the repair and regeneration of tissue comprising a network of branched channels. This network of channels provide a high degree of interconnectivity that aids in transferring nutrients to the center of the scaffold, thus encouraging and facilitating vascularization and, ultimately, tissue growth within the scaffold structure.

DETAILED DESCRIPTION OF THE INVENTION

The present invention provides a biocompatible foam scaffold for use in the repair and regeneration of tissue and a method of producing a scaffold in which a network of branched channels is embedded. The process involves a combination of phase separation and lyophilization in order to achieve this novel internal architecture.

According to one aspect of the present invention, a biocompatible porous scaffold is provided having a substantially continuous polymeric foam phase with a highly interconnected distribution of pores between about 50 and about 500 microns in diameter, in which is embedded a network of branched channels. The presence of the branched, channeled network in the porous scaffold provides passageways between the pores for the distribution of nutrients and the removal of waste. The resulting foams have a porosity of about 90%.

The branched channels provide interconnectivity that is useful for transmitting cell-to-cell, signaling molecules across the scaffold and allowing for the diffusion of nutrients through the scaffold. The channeled network also provides a patterned surface that is useful for guiding cell growth. In addition, the large surface area in the overall foam is ideal for cell seeding, cell growth and the production of extracellular matrices. Finally, the existence of channels in a three-dimensional structure encourages cell growth in the pores and further provides a means of infiltration into the interior of the scaffold by way of the channels.

In another aspect of the present invention, the polymer phase is bioabsorbable. Here, the scaffold undergoes biodegradation as the tissue grows and becomes incorporated in the site of the implantation.

Figure 1:
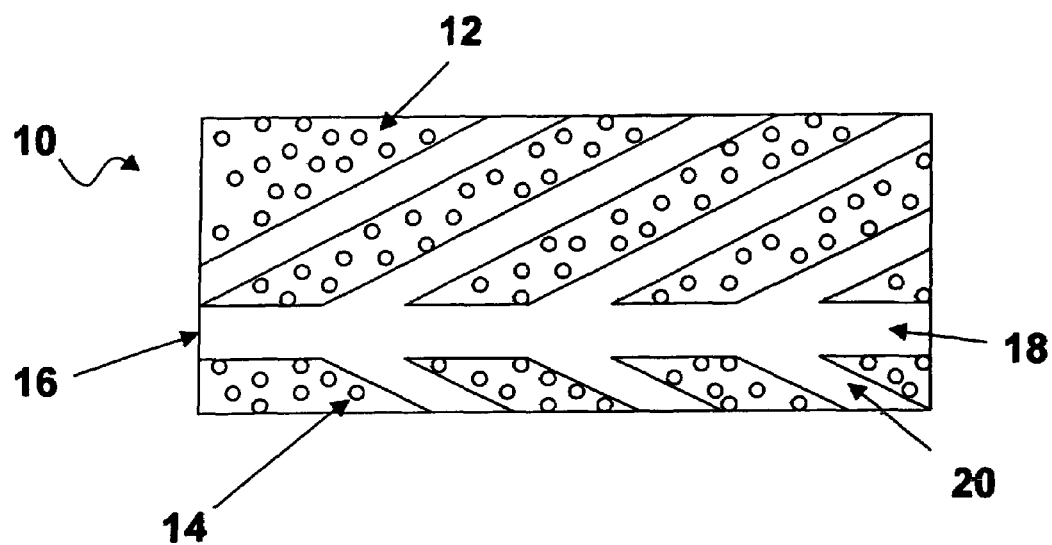
FIG. 1 is a sectional view of a foam scaffold according to the present invention.
Figure 2:
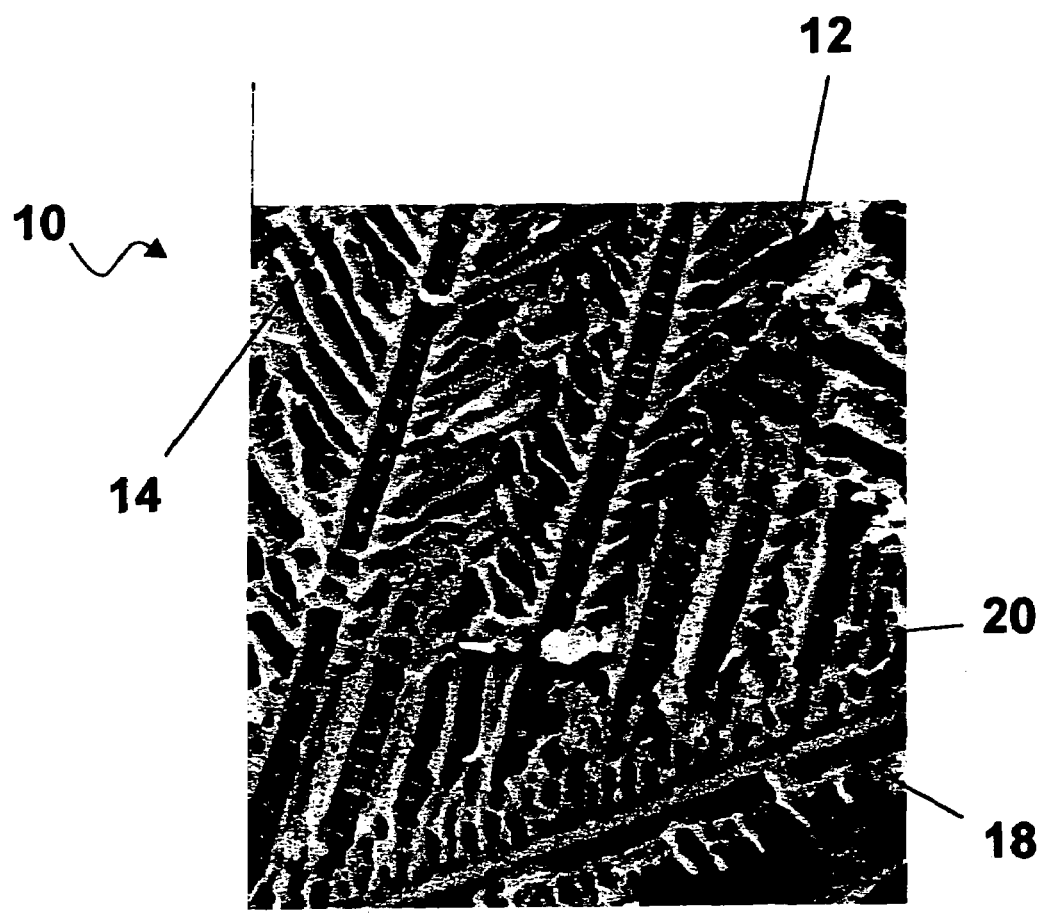
FIG. 2 is a scanning electron micrograph of a cross-section of a foam scaffold according to the present invention.

Referring to FIGS. 1 and 2, scaffold 10 includes a polymeric foam component 12 including pores 14 with open cell pore structure. Continuous branched channels 16 are embedded in foam component 12. These branched channels 16 have primary branches 18 as well as secondary branches 20. The branched channels 16 in the three-dimensional scaffold 10 structure encourages and facilitates cell growth in pores 14 and further provides a means for transferring nutrients to the center of scaffold 10, thus encouraging and facilitating vascularization into scaffold 10.

Biomedical polymers are suitable for use in the present invention. These types of polymers are biocompatible at the time of implant, causing no harm to living tissue. Preferably, the polymers should be biodegradable, where the polymer degradation products are biocompatible, non-toxic and physiologically compatible, and may also be bioabsorbable, or resorbed into living tissue. Additional parameters that play an important role include the mechanical properties of the material, especially its mechanical rigidity. High rigidity is advantageous where cells growing within the scaffold exert forces. It is also important that the biodegradation kinetics of the polymer match the rate of the healing process. Finally, from a processing standpoint, the thermal properties of the polymer are important to allow the polymer to retain mechanical integrity post-processing, e.g. a sufficiently high glass transition temperature to avoid pore/channel collapse upon solvent removal.

Polymers that can be used for the preparation of scaffolds for use in the repair and regeneration of tissue according to the present invention include polymers selected from the group consisting of aliphatic polyesters, poly(amino acids), polyalkylenes oxalates, polyamides, tyrosine derived polycarbonates, polyorthoesters, polyoxaesters, poly(anhydrides), and blends thereof. For the purpose of this invention aliphatic polyesters include, but are not limited to, homopolymers and copolymers of lactide (which includes lactic acid, D-, L- and meso lactide), glycolide (including glycolic acid), $\epsilon$-caprolactone, p-dioxanone (1,4-dioxan-2-one), trimethylene carbonate (1,3-dioxan-2-one), alkyl derivatives of trimethylene carbonate, $\delta$-valerolactone, $\beta$-butyrolactone, $\gamma$-butyrolactone, $\epsilon$-decalactone, hydroxybutyrate (repeating units), hydroxyvalerate (repeating units), 1,4-dioxepan-2-one (including its dimer 1,5,8,12-tetraoxacyclotetradecane-7,14-dione), 1,5-dioxepan-2-one, and 6,6-dimethyl-1,4-dioxan-2-one and blends thereof.

Elastomeric copolymers are also particularly useful in the present invention. These elastomeric copolymers will have an inherent viscosity in the range of about 1.0 dL/g to 4 dL/g, more preferably about 1.0 dL/g to 2.0 dL/g and most preferably about 1.0 dL/g to 1.7 dL/g as determined at 25° C. in a 0.1 gram per deciliter (g/dL) solution of polymer in hexafluoroisopropanol (HFIP). For the purpose of this invention, an "elastomeric copolymer" is defined as a polymer which, at room temperature, can be stretched repeatedly to at least about twice its original length and which, upon immediate release of stress, will return to approximately its original length.

Exemplary bioabsorbable, biocompatible elastomers include, but are not limited to, elastomeric copolymers of lactide (including L-lactide, D-lactide, blends thereof, and lactic acid polymers and copolymers) and $\epsilon$-caprolactone where the mole ratio of lactide to $\epsilon$-caprolactone is from about 30/70 to about 65/35, and more preferably from about 30/70 to about 50/50; elastomeric copolymers of lactide (including L-lactide, D-lactide, blends thereof, and lactic acid polymers and copolymers) and glycolide (including polyglycolic acid) where the mole ratio of lactide to glycolide is from about 75/25 to about 95/5.

The scaffolds of the present invention are foams prepared by the lyophilization of a polymer dissolved in a homogeneous mixture of components that act as solvents and non-solvents for the polymer. The process according to the present invention employs thermally induced phase separation to fabricate highly porous foam scaffolds comprising a network of branched channels embedded therein for the optimization of properties necessary to encourage and facilitate vascularization. Phase separation will occur by liquid-liquid demixing and crystallization based on the thermodynamics of the system. After lyophilization, the resulting foam contains an embedded network of branched channels resulting from the phase separation and crystallization of the non-solvent from the mixture during processing.

As mentioned above, the homogeneous mixture is comprised of several components, each of which has a particular relationship with the polymer. Specifically, the mixture comprises at least a first component in which the polymer is soluble, referred heretofore as the solvent, and a second component in which the polymer is not soluble, referred heretofore as the non-solvent.

Typically, the two components are liquids at, or slightly above, room temperature, and must also conform to certain criteria relative to one another. First, the solvent and non-solvent must be miscible; i.e. the solvent solubilizes both the polymer and the non-solvent. Second, the melting point of the non-solvent must be above that of the solvent. The higher melting point of the non-solvent allows phase separation of the non-solvent from the polymer mixture upon cooling. This is necessary to create the channels in the polymer foam. Finally, the freezing points of the solvent and non-solvent must be sufficiently disparate in order that the solid phase of the non-solvent is favorable, while the solid phase of the solvent is unfavorable, so that complete phase separation may occur in a given temperature range between the two freezing points. In this temperature range, phase separation occurs as the non-solvent crystallizes from the mixture. Due to colligative properties of the mixture, the solvent and non-solvent are expected to undergo a freezing point depression, the magnitudes of which are dependent on the properties of the pure solvent and non-solvent. As a result of this freezing point depression, a spread in the freezing points is also useful to allow the complete phase separation and crystallization of the non-solvent from the homogeneous mixture.

In processes for making the scaffolds of the present invention, a homogeneous mixture is made by combining polymer, solvent, and non-solvent. The mixture is then poured into a mold and placed in a lyophilizer. The formation of the channeled scaffold is a one-step process that relies on the properties of the respective components of the mixture and the lyophilization cycle. The first segment of the cooling cycle involves a ramping-down to a temperature below the depressed freezing point of the non-solvent, but above that of the solvent. The temperature is held while crystals of the non-solvent begin to nucleate and grow. This phase separation may occur in the form of dendrites of the non-solvent that grow in the mixture, creating a branch-like structure within the mixture. Since the polymer is not soluble in the non-solvent, the dendrites of non-solvent do not contain polymer. The dendrites of non-solvent growing in the polymer solution act as placeholders for the branched channel network structure that will result upon the sublimation of the non-solvent.

Once the non-solvent has crystallized, the temperature is decreased below the freezing point of the solvent. At this point, the polymer/solvent mixture solidifies. The degree of crystallinity of this solid phase depends on the rate of temperature decrease. Whether amorphous, crystalline, or some combination thereof, this solidified polymer/solvent mixture is responsible for foam formation.

The solid mixture sublimes by way of the lyophilization cycle as vacuum is applied to the frozen sample, leaving behind a polymer foam with pores forming as the solvent sublimes and branched channels forming in the foam as the non-solvent sublimes.

Non-solvent crystallization during liquid-liquid demixing occurs with the correct selection of solvents and processing conditions. A mixture of at least one component which is a solvent and at least one component which is a non-solvent for the polymer is employed. As mentioned above, the solvent and non-solvent must be miscible. Further, the proportions and mixing of the two components are chosen so as to retain solubility of the polymer in the solvent despite its insolubility in the non-solvent. This yields a uniform, homogenous mixture.

Solvents useful in the present invention include, but are not limited to, dimethyl carbonate (DMC; m.p. 5° C.), 1,4-dioxane (m.p. 12° C.) and diethyl carbonate (m.p. −43° C.). Non-solvents in which the polymer is insoluble that are suitable for use include, but not limited to, alcohols such as t-butanol (m.p. 25° C.), tert-amyl alcohol (m.p. −12° C.) 3,3 dimethyl-2 butanol (m.p. −5° C.), octanol (m.p. −15° C.), nonanol (m.p. −8° C.), decanol (m.p. 7° C.), n-decanol (m.p. 11° C.), and dodecanol (m.p. 22-26° C.). It is critical that the polymer be soluble in the overall solvent/non-solvent mixture.

The melting point of the non-solvent must be higher than that of the solvent. In addition, the disparity in melting points between the two solvents should be sufficiently large to allow thorough crystallization of the non-solvent during liquid/liquid demixing step of the process. Preferably, the disparity in melting points is greater than about 20° C. A preferred solvent/non-solvent pair meeting the above requirements are dimethyl carbonate (DMC; m.p. 5° C.) which is a solvent for the disclosed polymers, and t-butanol (m.p. 25° C.), a non-solvent for the disclosed polymers.

Combining the polymer, solvent and non-solvent can be accomplished in two ways. The polymer may first be completely dissolved in the solvent followed by the addition of the non-solvent. Alternatively, the solvent and non-solvent may be mixed followed by the addition of polymer. If the non-solvent is added to the polymer solution, then it is added into a constantly agitated polymer solution at a rate effective to avoid localized precipitation of the polymer in the homogeneous mixture. The weight ratio of the non-solvent to the total volume of the solvent and non-solvent is preferably between about 1 to about 50 weight percent and more preferable between about 15 to about 30 weight percent. The polymer concentration in the solvent mixture is preferably between about 0.5 and about 25 weight percent and more preferably between about 2.5 and about 10 weight percent.

Alternatively, the method of the present invention can also be used to make a porous scaffold of a first polymer with branched channels of a second porous polymer embedded within the structure. This structure is created if the second polymer is insoluble in the solvent, and soluble in the non-solvent. This mixture creates dual solid-liquid phase transformation processes occurring within the same system. Again, the two components must be miscible, but the two polymers used in the system must only be soluble in one of the components, i.e. its respective solvent. Upon cooling the system, the temperature is held for a sufficient time to allow the first component to crystallize, thus forcing a solid-liquid phase transformation and precipitation of the first polymer in a dendritic branched fashion. After complete crystallization of the first component, the temperature is then lowered until the second solid-liquid phase transformation occurs. Sublimation of the system leaves behind a branched foam structure of one polymer embedded within a second foam structure of another polymer.

The porous polymer scaffolds can be molded or cut to shape for tissue engineering and tissue guided regeneration applications. Cellular pre-seeding can be used prior to implantation or the scaffold can be used in an acellular fashion due to the structure of the scaffold that allows generous cellular ingrowth. The scaffold serves both as a physical support and an adhesive substrate for isolated cells during in vitro culture and subsequent implantation. As the transplanted cell populations grow, the cells function normally and begin to secrete their own extracellular matrices (ECM) which allows the scaffold to mimic the ECM of an organ. The porous polymer scaffold may, therefore, be used as an external scaffolding for the support of in vitro culturing of cells for the creation of external support organs. In all cases, the scaffold polymer is selected to degrade as the need for the artificial support diminishes.

In applications where the tissue shape is integral to tissue function, the polymer scaffold may be molded to have the appropriate dimensions. Any crevices, apertures or refinements desired in the three-dimensional structure can be created by fashioning the matrix with scissors, a scalpel, a laser beam or any other cutting instrument. Scaffold applications include the regeneration of tissues such as adipose, pancreatic, cartilaginous, osseous, musculoskeletal, nervous, tendenous, hepatic, ocular, integumeary, arteriovenous, urinary or any other tissue forming solid or hollow organs.

The scaffold may also be used in transplantation as a matrix for dissociated cell types. These include fibrochondrocytes, adipocytes, pancreatic Islet cells, osteocytes, osteoblasts, myeloid cells, chondrocytes, hepatocytes, exocrine cells, cells of intestinal origin, bile duct cells, parathyroid cells, nucleus pulposus cells, annulus fibrosis cells, thyroid cells, endothelial cells, smooth muscle cells, fibroblasts, meniscal cells, sertolli cells, cells of the adrenal-hypothalamic-pituitary axis, cardiac muscle cells, kidney epithelial cells, kidney tubular cells, kidney basement membrane cells, nerve cells, blood vessel cells, cells forming bone and cartilage, smooth muscle cells, skeletal muscle cells, ocular cells, integumentary cells, keratinocytes, peripheral blood progenitor cells, fat-derived progenitor cells, glial cells, macrophages, mesenchymal stem cells, embryonic stem cells, stem cells isolated from adult tissue, genetically engineered cells, and combinations thereof. Pieces of tissue can also be used, which may provide a number of different cell types in the same structure.

Allogeneic or autologous cells may be used and are dissociated using standard techniques and seeded onto or into the foam scaffold. If the cells are seeded onto the scaffold, seeding may take place prior to, or after, the scaffold is implanted. If the cells are added after implantation, the added benefit is that cells are placed into the scaffold after it has had an opportunity to vascularize and be incorporated into the implant site. Methods and reagents for culturing cells in vitro and implantation of a tissue scaffold are known to those skilled in the art.

After fabrication, scaffolds can be further modified to increase effectiveness of the implant. For example, the scaffolds can be coated with bioactive substances that function as receptors or chemoattractors for a desired population of cells. The coating can be applied through absorption or chemical bonding and may be designed to deliver therapeutic or medicated additives in a controlled fashion. In addition, since the lyophilization of the foam takes place at low temperatures, thermally sensitive additives can be used without concern of degradation during polymer processing. The additive may be released by a bioerosion of the polymer phase or by diffusion from the polymer phase. Alternative to release, the additive may simply migrate to the polymer surface of the scaffold structure where it is active.

Depending on the additive and the nature of the components used in the system, the additive may be added to the pre-blended mixture or it may be added first to the component in which it is most soluble before adding another component. The additive may be provided in a physiologically acceptable carrier, excipient, or stabilizer, and may be provided in sustained release or timed release formulations. The additives may also incorporate biological agents to facilitate their delivery, such as antibodies, antibody fragments, growth factors, hormones, demineralized bone matrix, or other targeting moieties, to which the additives are coupled.

Acceptable pharmaceutical carriers for therapeutic use are well known in the pharmaceutical field. Such materials are non-toxic to recipients at the dosages and concentrations employed, and include diluents, solubilizers, lubricants, suspending agents, encapsulating materials, solvents, thickeners and dispersants. Also acceptable are buffers such as phosphate, citrate, acetate and other organic acid salts. Anti-oxidants such as ascorbic acid, preservatives, low molecular weight peptides (less than about 10 residues), such as polyarginine, proteins such as serum albumin, gelatin or immunoglobulins may also be used. The pharmaceutical carriers can also include hydrophilic polymers such as poly(vinylpyrrolindinone), amino acids such as glycine, glutamic acid, aspartic acid or arginine, monosaccharides, disaccharides, and other carbohydrates including cellulose or its derivatives, glusocse, mannose or dextrines. Chelating agents such as EDTA, sugar alcohols, such as mannitol or sorbitol, counterions such as sodium and/or non-ionic surfactants such as tween, pluronics or PEG are all acceptable carriers as well.

As mentioned, the coating can be applied through absorption or chemical bonding, the latter taking place by covalently binding the additive to a pendent free carboxylic acid group on the polymer. For example, moieties having reactive functional groups or being derivatized to contain active functional groups may be reacted with polymer pendent free carboxylic acid groups to form a polymer conjugate. If the additive is active in the conjugate form, then conjugates that are resistant to hydrolysis are utilized. The opposite is true if the additive is inactive in the conjugate form in which case the conjugate used is hydrolyzable.

The amount of additive incorporated into the porous polymer scaffold is chosen to provide optimal efficacy to the subject in need of treatment, typically a mammal. A dose and method of administration will vary from subject to subject and be dependent upon such factors as the type, sex, weight, and diet of the mammal being treated. Other factors include concurrent medication, the particular compounds employed, overall clinical condition, and other factors that those skilled in the art will recognize. The porous polymer scaffolds can be utilized in vitro or in vivo as tissue engineering and tissue guided regeneration scaffold in mammals such as primates, including humans, sheep, horses, cattle, pigs, dogs, cats, rats, and mice. As the polymers used in this invention are typically suitable for storage at ambient or refrigerated temperatures, the polymer-drug combinations of this invention may be prepared for storage under conditions suitable for the preservation of drug activity. Sterility is also an issue for polymer scaffolds to be used in tissue engineering and tissue guided regeneration applications and may be accomplished using conventional methods such as treatment with gases, heat, or irradiation.

Additives suitable for use with the present invention include biologically or pharmaceutically active compounds. Examples of biologically active compounds include cell attachment mediators, such as peptide containing variations of the "RGD" integrin binding sequence known to affect cellular attachment, biologically active ligands, and substances that enhance or exclude particular varieties of cellular or tissue ingrowth. Examples of such substances include integrin binding sequence, ligands, bone morphogenic proteins, epidermal growth factor, fibroblast growth factor, platelet-derived growth factor, IGF-I, IGF-II, TGF-βI-III, growth differentiation factor, parathyroid hormone, vascular endothelial growth factor, hyaluronic acid, gylcoprotein, lipoprotein, and the like.

Examples of pharmaceutically active compounds include antiinfectives, analgesics, anorexics, antihelmintics, antiarthritics, antiasthmatics, anticonvulsants, antidepressants, antidiuretics, antidiarrheals, antihistamines, antiinflammatory agents, antimigraine preparations, antinauseants, antineoplastics, antiparkinsonism drugs, antipruritics, antipsychotics, antipyretics, antispasmodics, anticholinergics, sympathomimetics, xanthine derivatives, calcium channel blockers, beta-blockers, antiarrhythmics, antihypertensives, diuretics, vasodilators, central nervous system stimulants, decongestants, hormones, steroids, hypnotics, immunosuppressives, muscle relaxants, parasympatholytics, psychostimulants, sedatives, tranquilizers, naturally derived or genetically engineered proteins, polysaccharides, glycoproteins, or lipoproteins, oligonucleotides, antibodies, antigens, cholinergics, chemotherapeutics, hemostatics, clot dissolving agents, radioactive agents and cystostatics, and the like. Therapeutically effective dosages may be determined by in vitro or in vivo methods. For each particular additive, individual determinations may be made to determine the optimal dosage required. The determination of effective dosage levels to achieve the desired result will be within the realm of one skilled in the art. The release rate of the additives may also be varied within the routine skill in the art to determine advantageous profile, depending on the therapeutic conditions to be treated.

A typical additive dosage might range from about 0.001 mg/kg to about 1000 mg/kg, preferably from about 0.01 mg/kg to about 100 mg/kg, and more preferably from about 0.10 mg/kg to about 20 mg/kg. The additives may be used alone or in combination with other therapeutic or diagnostic agents.

The invention will be better understood by reference to the following non-limiting examples.

EXAMPLE 1

A mixture to be lyophilized was first prepared. The mixture was composed of a 60/40 copolymer of PLA/PCL (I.V. of 1.7 dL/g at 25° C. in a 0.1 g/dL solution of HFIP), and dimethyl carbonate, a solvent for 60/40 PLA/PCL, in a 95/5 weight ratio. The polymer and solvent were placed into a flask that was then placed into a water bath and heated to 70° C. The solution was heated and stirred for 5 hours. Afterwards, the solution was filtered using an extraction thimble (extra coarse porosity, type ASTM 170-220(EC)) and stored in the flask.

Twenty milliliters of t-butanol was added to 80 ml of the polymer solution in a dropwise fashion to form an 80/20 volumeric mixture. The polymer solution was constantly agitated during the dropwise addition of t-butanol.

Twenty milliliters of the 80/20 mixture was poured into a 50-ml recrystallization dish. The dish was placed on the shelf of a pre-cooled (20° C.) laboratory scale lyophilizer (Model Freeze Mobile G from Virtis Company (Gardiner, N.Y.), and was subjected to the following freeze dry sequence: cool at 2.5° C./min to 0° C., hold 40 minutes; cool at 2.5° C./min to −10° C., hold 120 minutes; cool at 2.5° C./min to −50° C., hold 15 minutes; hold at −48° C. for an additional 60 minutes; turn on the condenser; turn on vacuum pump once condenser reaches −40° C.; hold until vacuum in chamber is 150 mT and vacuum in foreline is 100 mT, then hold an additional 60 minutes; warm at 2.5° C./min to −30° C., hold 60 minutes; warm at 2.5° C./min to −15° C., hold 60 minutes; warm at 2.5° C./min to 0° C., hold 60 minutes; warm at 2.5° C./min to 15° C., hold 60 minutes; warm at 2.5° C./min to 22° C., hold 60 minutes.

As the temperature decreased to −10° C., dendritic crystals grew in the solution as the t-butanol phase separated from the mixture. The remaining polymer in dimethyl carbonate was frozen at −50° C. The foam was formed as the dimethyl carbonate sublimed and the channels were formed as the dendritic crystals of t-butanol sublimed.

Scanning electron micrographs (SEMSs) showed the average pore diameter of the foam to be in the range of 50 to 400 microns and the channels to have an average diameter in the range of 0.5 to 1.0 mm.

We claim:

1. A process for making biomedical, biocompatible scaffolds suitable for use in the repair and regeneration of tissue, comprising:

preparing a homogenous mixture comprising a synthetic, biocompatible polymer, a solvent in which said polymer is soluble, and a non-solvent in which said polymer is not soluble, wherein said solvent and said non-solvent are miscible, and wherein the freezing point of said non-solvent is higher than the freezing point of said solvent, placing said homogenous mixture in a mold or other device suitable for preparing foam scaffolds suitable for use in repair and regeneration of tissue, cooling said homogenous mixture to a first temperature effective to freeze said non-solvent;

maintaining said first temperature for a sufficient period of time effective to allow phase separation of said non-solvent from said homogenous mixture and to generate dendritic crystals;

cooling said homogenous mixture to a second temperature sufficient to form a solid; and, removing said solvent and said non-solvent from said solid to provide a biocompatible, porous foam scaffold which comprises a network of branched channels.

2. The process of claim 1 wherein said polymer is bioabsorbable.

3. The process of claim 2 wherein said bioabsorbable polymer is selected from the group consisting of aliphatic polyesters, poly(amino acids), polyalkylenes oxalates, polyamides, tyrosine derived polycarbonates, polyorthoesters, polyoxaesters and poly(anhydrides).

4. The process of claim 3 wherein said polymer comprises an aliphatic polyester selected from the group consisting of homopolymers and copolymers of lactide, lactic acid, glycolide, glycolic acid, ε-caprolactone, p-dioxanone, trimethylene carbonate, alkyl derivatives of trimethylene carbonate, δ-valerolactone, β-butyrolactone, γ-butyrolactone, ε-decalactone, hydroxybutyrate, hydroxyvalerate, 1,4-dioxepan-2-one, 1,5,8,12-tetraoxacyclotetradecane-, 14-dione, 1,5-dioxepan-2-one, and 6,6-dimethyl-1,4-dioxan-2-one.

5. The process of claim 4 wherein said aliphatic polyester comprises an elastomer selected from the group consisting of copolymers of lactide and ε-caprolactone, lactide and glycolide, and blends thereof.

6. The process of claim 5 wherein said copolymer of lactide and ε-caprolactone comprises a mole ratio of lactide to ε-caprolactone from about 30/70 to about 50/50.

7. The process of claim 5 wherein said copolymer of lactide and glycolide comprises a mole ratio of lactide to glycolide from about 75/25 to about 95/5.

8. The process of claim 3 wherein said solvent is selected from the group consisting of dimethyl carbonate, 1,4-dioxane and diethyl carbonate.

9. The process of claim 8 wherein said non-solvent is selected from the group consisting of t-butanol, tert-amyl alcohol, 3,3 dimethyl-2 butanol, octanol, nonanol, decanol, n-decanol and dodecanol.

* * * * *

UNITED STATES PATENT AND TRADEMARK OFFICE
CERTIFICATE OF CORRECTION

PATENT NO. : 7,674,408 B2  Page 1 of 1
APPLICATION NO. : 11/230220
DATED : March 9, 2010
INVENTOR(S) : Kelly R. Brown, Mora C. Melican and Iksoo Chun It is certified that error appears in the above-identified patent and that said Letters Patent is hereby corrected as shown below:

Title Page, Item (54) and at Column 1, lines 1 and 2,
Title on Issue Patent is "CHANNELED BIOMEDICAL FOAMS __AN__ METHOD FOR PRODUCING SAME"
Correct Title should be: "CHANNELED BIOMEDICAL FOAMS __AND__ METHOD FOR PRODUCING SAME"

Signed and Sealed this

Eighteenth Day of May, 2010

David J. Kappos
*Director of the United States Patent and Trademark Office*